(12) United States Patent
Guala

(10) Patent No.: US 8,048,038 B2
(45) Date of Patent: Nov. 1, 2011

(54) VALVE CONNECTOR FOR MEDICAL LINES

(75) Inventor: Gianni Guala, Turin (IT)

(73) Assignee: Industrie Borla S.p.A., Moncalieri (Torino) (IT)

( * ) Notice: Subject to any disclaimer, the term of this patent is extended or adjusted under 35 U.S.C. 154(b) by 166 days.

(21) Appl. No.: 11/687,188

(22) Filed: Mar. 16, 2007

(65) Prior Publication Data

US 2007/0218757 A1 Sep. 20, 2007

(30) Foreign Application Priority Data

Mar. 17, 2006 (IT) .............................. TO2006A0206

(51) Int. Cl.
- A61M 5/00 (2006.01)
- A61M 5/14 (2006.01)
- F16K 31/44 (2006.01)

(52) U.S. Cl. ....................... 604/246; 604/256; 251/149.6

(58) Field of Classification Search .................. 604/246, 604/247, 249, 256, 283, 533, 905; 251/149.1
See application file for complete search history.

(56) References Cited

U.S. PATENT DOCUMENTS

| | | | |
|---|---|---|---|
| 5,242,342 A | | 9/1993 | Silverman |
| 5,439,451 A | * | 8/1995 | Collinson et al. ............. 604/247 |
| 5,514,116 A | * | 5/1996 | Vaillancourt et al. ......... 604/537 |
| 5,676,346 A | * | 10/1997 | Leinsing .................... 251/149.1 |
| 5,699,821 A | * | 12/1997 | Paradis ............................. 137/1 |
| 5,700,248 A | | 12/1997 | Lopez |
| 5,820,601 A | * | 10/1998 | Mayer ...................... 604/167.02 |
| 6,039,302 A | * | 3/2000 | Cote et al. .................. 251/149.1 |
| 6,050,978 A | * | 4/2000 | Orr et al. .................... 251/149.1 |
| 6,079,432 A | * | 6/2000 | Paradis ............................. 137/1 |
| 6,682,509 B2 | | 1/2004 | Lopez |
| 6,706,022 B1 | | 3/2004 | Leinsing et al. |
| 6,755,391 B2 | * | 6/2004 | Newton et al. ............. 251/149.6 |

(Continued)

FOREIGN PATENT DOCUMENTS

WO 98/50106 A1 11/1998

(Continued)

OTHER PUBLICATIONS

European Search Report for Application #PCT/IB2005/002206 dated Jul. 13, 2007.

Primary Examiner — Theodore Stigell
Assistant Examiner — William Carpenter
(74) Attorney, Agent, or Firm — Heslin Rothenberg Farley & Mesiti P.C.; Victor A. Cardona, Esq.

(57) ABSTRACT

A valve connector for medical infusion lines including an external tubular body with an inlet end and an outlet end, an internal hollow spike and an intermediate sealing member including a head with pre-slit and an elastic hollow element formed with fluid-tight members in contact with the hollow spike and with an elastic thrust means, which tends to maintain the elastic head in a closed condition. The elastic thrust means comprises a base part joined to the elastic hollow element of the sealing member through a generally transverse annular wall, which, during axial displacement of the elastic head from the closed condition to the open condition, bends within an annular chamber defined between the base part and a portion with conical surface of the hollow spike.

18 Claims, 13 Drawing Sheets

U.S. PATENT DOCUMENTS

| | | | |
|---|---|---|---|
| 6,991,215 B2 * | 1/2006 | Kiehne | 251/149.6 |
| 7,296,782 B2 * | 11/2007 | Enerson et al. | 251/149.7 |
| 7,396,348 B2 * | 7/2008 | Newton et al. | 604/256 |
| 2005/0038397 A1 * | 2/2005 | Newton et al. | 604/249 |

FOREIGN PATENT DOCUMENTS

| | | |
|---|---|---|
| WO | WO2005/011799 A1 | 2/2005 |
| WO | 2006/013433 | 2/2006 |
| WO | WO2006/013433 A1 | 2/2006 |
| WO | WO 2006013433 A1 * | 2/2006 |

* cited by examiner

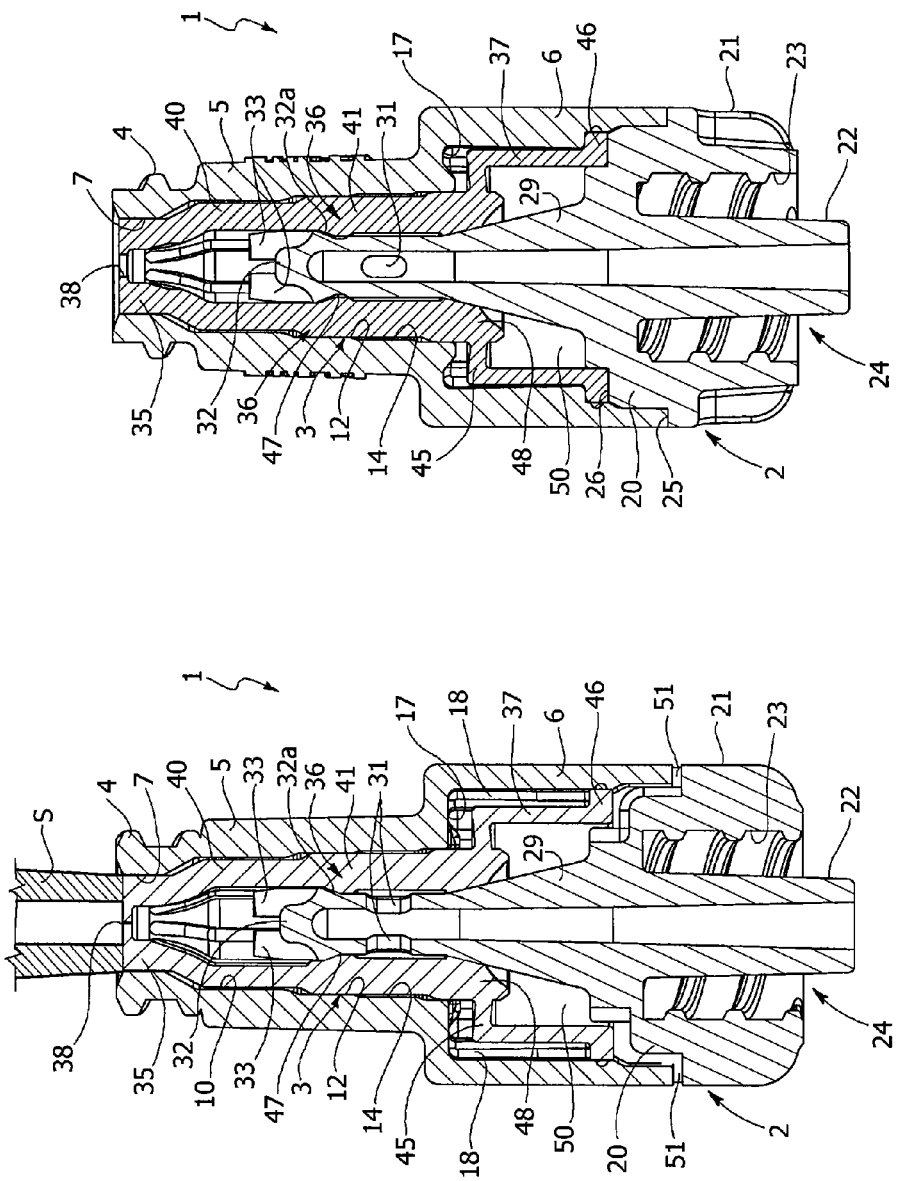

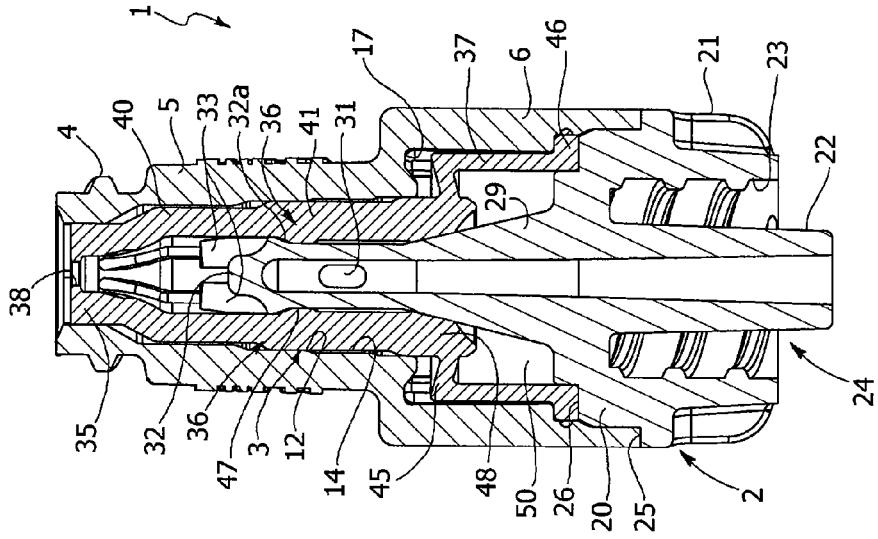
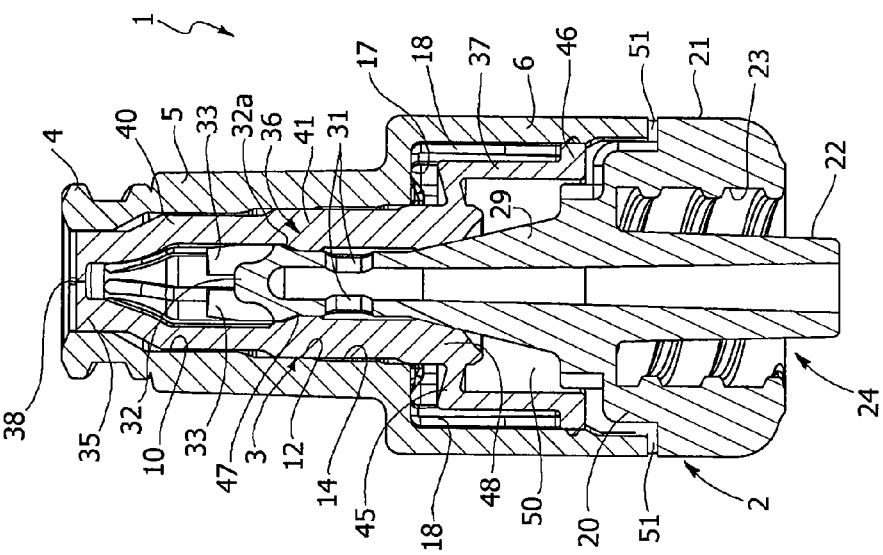

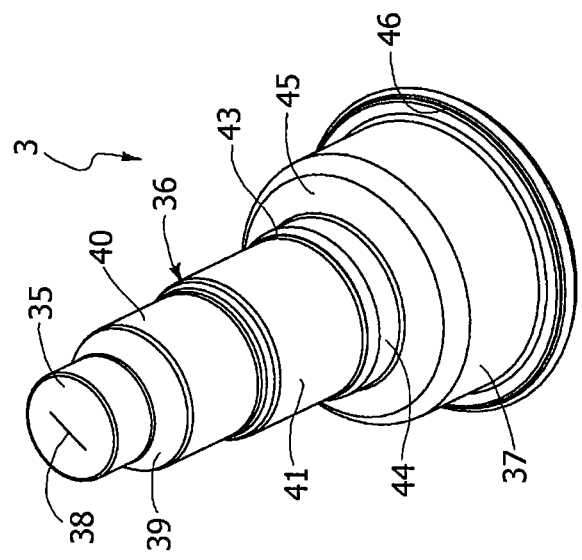
FIG. 17
FIG. 18
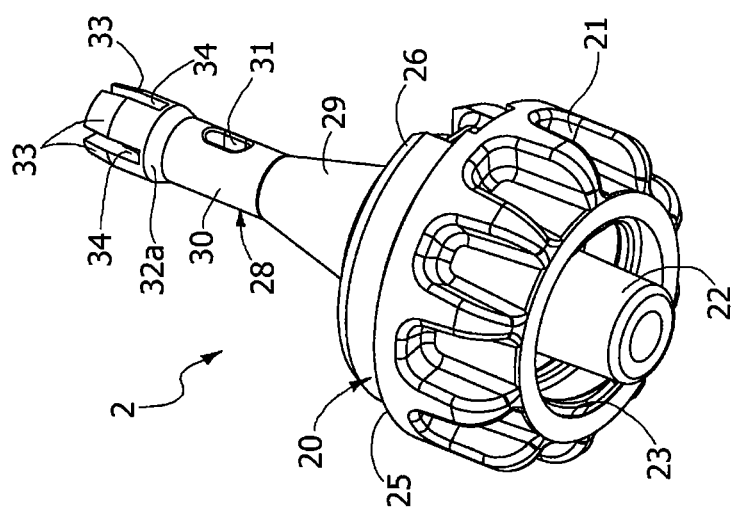
FIG. 16

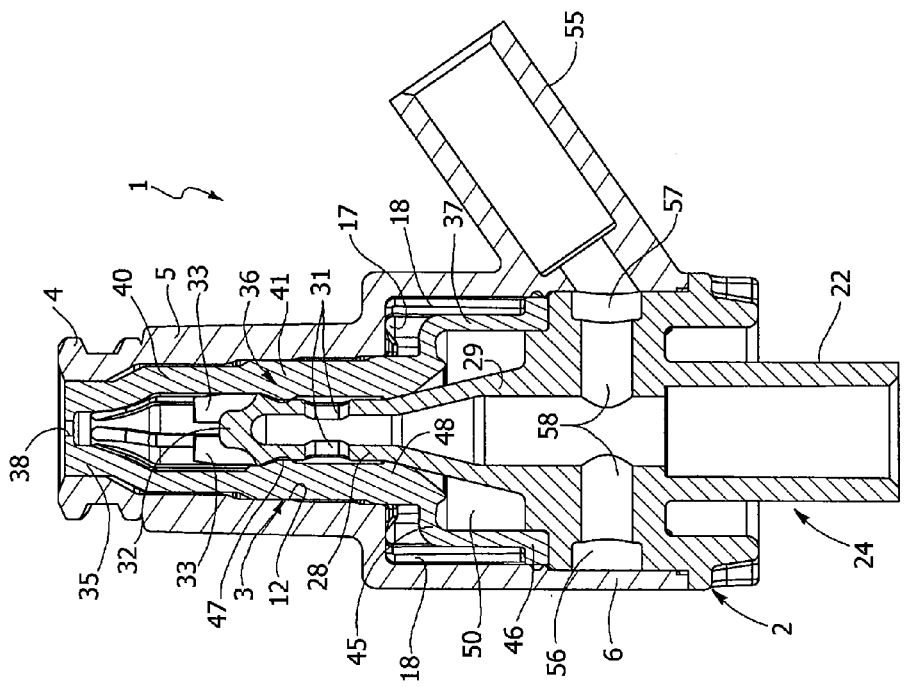
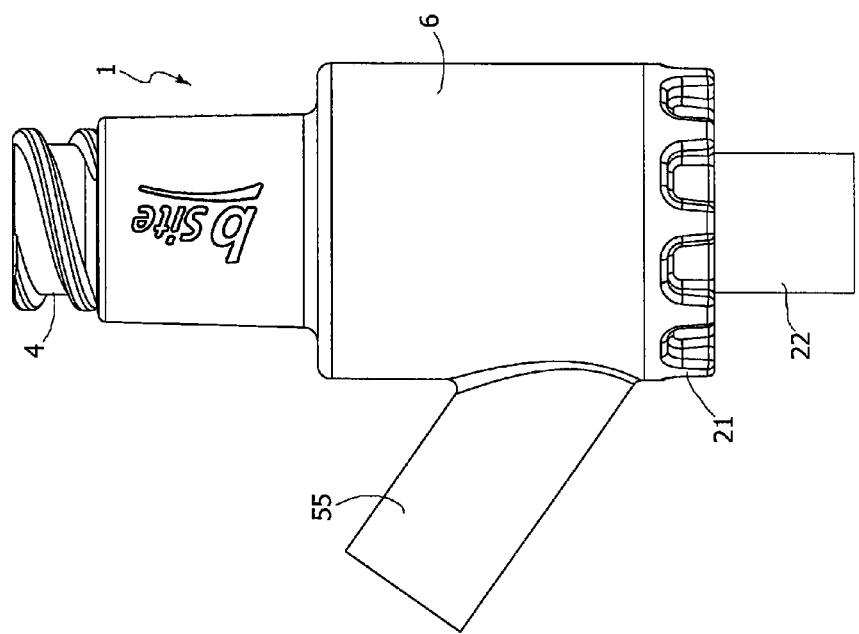

VALVE CONNECTOR FOR MEDICAL LINES

CROSS-REFERENCE TO RELATED APPLICATIONS

This application claims priority from Italian Patent Application No. TO2006A000206, filed on Mar. 17, 2006, the entire disclosure of which is incorporated herein by reference.

FIELD OF THE INVENTION

The present invention relates to valve connectors for medical lines, for example lines for infusion by means of an introducer for introducing a fluid infusion substance, typically a luer connector or luer-lock connector, for example of a needleless syringe.

STATE OF THE ART

Valve connectors of this type are known, for example, from the documents Nos. U.S. Pat. No. 5,242,342, U.S. Pat. No. 5,676,346, U.S. Pat. No. 6,706,022, U.S. Pat. No. 5,700,248 and U.S. Pat. No. 6,682,509.

More in particular, the documents Nos. U.S. Pat. No. 5,700,248 and U.S. Pat. No. 6,682,509 describe a valve connector according to the preamble of Claim 1, in which a tubular body is provided having a cavity, an inlet end provided for engagement of an introducer of liquid, and an outlet end. A hollow spike is set axially within the cavity of the tubular body and has a closed tip facing the inlet end of the tubular body and set at an axial distance from this. The hollow spike is in communication with the outlet end of the tubular body and has at least one side hole set at a distance from its closed tip for communication with the cavity of the tubular body. The connector moreover includes an elastic sealing member, which comprises an elastic head having a pre-slit and normally set in a condition of closing (or deactivated condition) within the inlet end of the tubular body, in which the pre-slit is closed. The elastic head is displaceable axially against the closed tip of the hollow spike as a result of insertion of the introducer into the inlet end of the tubular body in order to interact with said tip, assuming an elastically deformed configuration of opening (activated condition), in which the pre-slit opens. The sealing member of the valve connector moreover includes an elastic hollow element joined to the head, set between the tubular body and the hollow spike and having sealing means in contact with said hollow spike for isolating the aforesaid at least one side hole from the cavity of the tubular body when the head is set in the undeformed condition of closing. The elastic hollow element includes an elastic thrust means, which tends to maintain the head of the sealing member in the aforesaid condition of closing.

Valve connectors of the above type must meet a series of fundamental requisites, since their use is frequently critical for survival of patients that make use thereof.

In the first place, closing of the inlet end of the tubular body performed by the head of the sealing member must be substantially fluid-tight so as to ensure a total anti-bacterial barrier, even following upon repeated opening and re-closing of the valve connector.

In the second place, the operation of opening and re-closing the communication between the inlet end and the outlet end of the connector at the moment of insertion and extraction, respectively, of the introducer must be altogether reliable and repeatable, without the minimum risk of malfunctioning, which could lead to serious risks for the patient connected to the valve connector. For this reason, the number of moving mechanical members of the valve connector must be as small as possible.

In the third place, these connectors must be able to support effectively possible overpressures that may be generated inside them in use, and in the condition of closing (or deactivated condition) guarantee an effective fluid-tightness at positive and negative pressures.

Finally, the above valve connectors must be easily cleanable and disinfectable ("swabbable") at the inlet end, typically using a swab soaked in disinfectant.

In the case of the valve connectors known from the aforementioned documents Nos. U.S. Pat. No. 5,700,248 and U.S. Pat. No. 6,682,509, opening of the communication between the inlet end of the tubular body and the outlet end, through the side hole or holes of the hollow spike at the moment of engagement of the introducer, is performed following upon traversal of the pre-slit of the elastic head by the tip of the hollow spike. In other embodiments, known for example from the documents Nos. WO-2005/011799 and WO-2006/013433 (filed in the name of the present applicant), the closed tip of the hollow spike is, instead, shaped so as to cause the head of the sealing member to assume the aforesaid configuration of opening, without traversal of the pre-slit.

In all the above known solutions, the elastic thrust means of the elastic hollow element of the sealing member typically has a corrugated or bellows-like wall, so that axial compression thereof produces a collapse like that of a concertina, or else an uncorrugated, but in any case axially collapsible, wall. The axial compression or collapse of the elastic hollow element causes the elastic head of the sealing member to slide along the hollow spike until the corresponding sealing means open the communication between the cavity of the tubular body and the side hole or holes of the hollow spike, i.e., between the inlet end and the outlet end of the tubular body.

The known solutions described above are not free from drawbacks, in some cases as regards the reliability and repeatability of restoration of the condition of closing of the sealing member following upon removal of the introducer from the connector, and in other cases as regards the permanence of a positive or negative pressure within the connector following upon said re-closing. Furthermore, on account of the conformation of the elastic thrust means of the sealing member, the body of said known connectors generally has a considerable axial extension that it would instead be desirable to avoid.

SUMMARY OF THE INVENTION

The purpose of the present invention is to overcome the aforesaid drawbacks, and said purpose is basically achieved thanks to the fact that the elastic thrust means of the sealing member comprises a base part of said elastic hollow element having a generally cylindrical axial wall, set at a radial distance from said spike so as to define with this an annular chamber, said base part being joined to said elastic hollow element through a generally transverse annular wall, which, during the axial displacement of the elastic head from the condition of closing to the condition of opening, bends within said annular chamber.

Conveniently, the aforesaid generally transverse wall bends, undergoing deformation due to tensile stress.

Thanks to this idea of solution the valve connector according to the invention presents an improved degree of reliability, guaranteeing a prompt return of the sealing member to the closed condition even following upon repeated opening, with appreciably reduced overall axial dimensions of the connector. The valve connector is made up of a minimal number of parts, and hence can be produced in a relatively simple and inexpensive way, and moreover—thanks to further solutions that will be clarified in what follows—is able to ensure substantial absence of overpressures or negative pressure inside it during the steps of transition between the condition of opening and that of closing.

In one embodiment, the tubular body of the connector according to the invention is advantageously formed with a tubular side Y-connector.

BRIEF DESCRIPTION OF THE DRAWINGS

The invention will now be described in detail with reference to the annexed plate of drawings, which is provided purely by way of non-limiting example and in which:

FIG. 3 is a schematic view in axial cross section of the valve connector represented in a first condition;

FIG. 4 is a view similar to that of FIG. 3 but rotated through 90°;

FIGS. 5-6, 7-8, 9-10 and 11-12 are views similar to those of FIGS. 3 and 4, respectively, which illustrate the valve connector in different successive operating conditions;

FIG. 16 is a perspective view of a second component of the tubular connector;

FIG. 17 is a perspective view of a third component of the tubular connector;

FIG. 18 is a view in elevation of the component of FIG. 17;

FIG. 20 is a view in elevation of a variant of the valve connector according to the invention;

FIG. 21 is an axial cross-sectional view of the variant of FIG. 20;

DETAILED DESCRIPTION OF THE INVENTION

The first embodiment of the valve connector for medical infusion lines according to the invention, represented in FIGS. 1 to 19, basically comprises three components: an external tubular body 1, an internal hollow spike 2, set axially within the cavity of the tubular body 1, and an elastic sealing member 3. Typically, the tubular body 1 and the hollow spike 2 are made of rigid moulded plastic material, whilst the sealing member 3 is made of an elastic material, for example silicone rubber.

Figure 1:
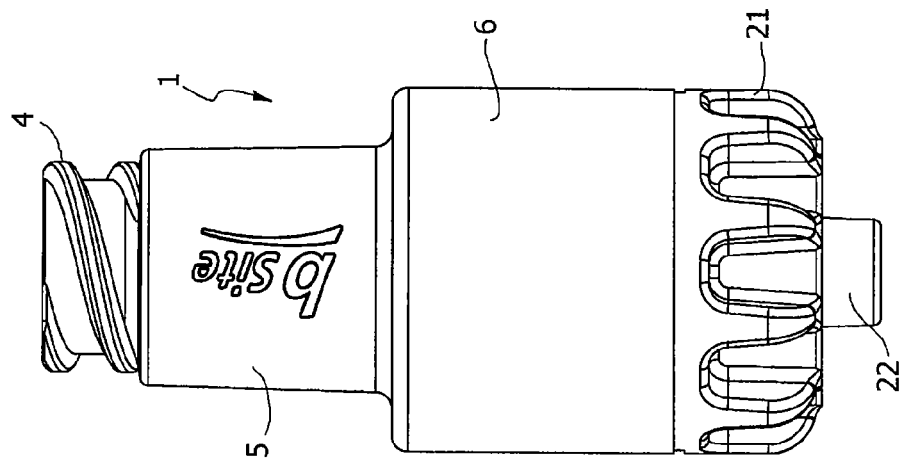
FIG. 1 is a schematic perspective view of a valve connector for medical lines according to a first embodiment of the invention.
Figure 2:
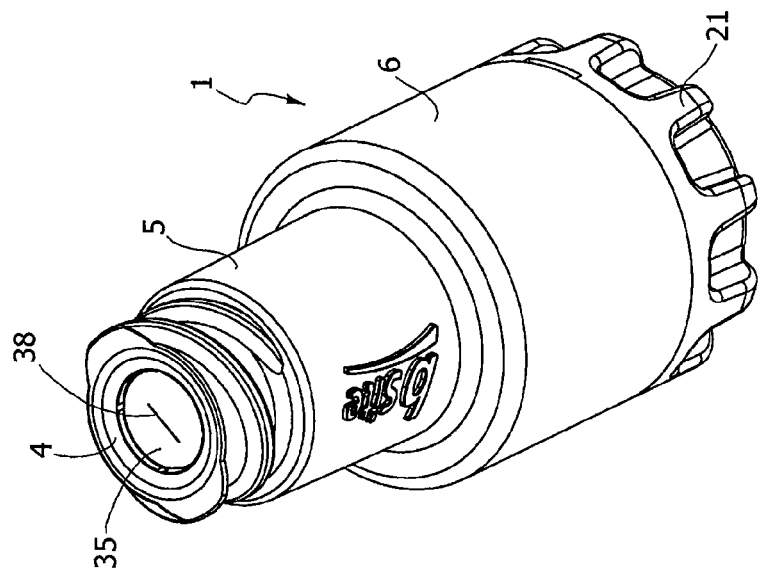
FIG. 2 is a view of the valve connector in elevation.
Figure 7:
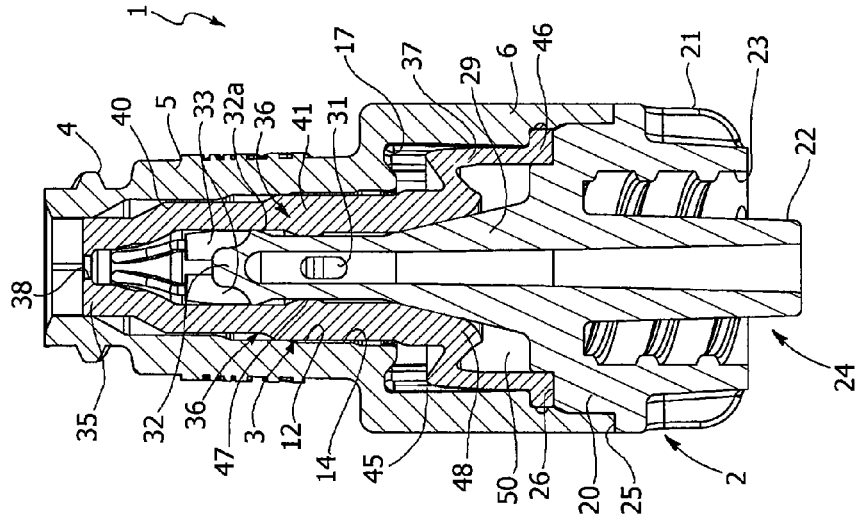
Figure 8:
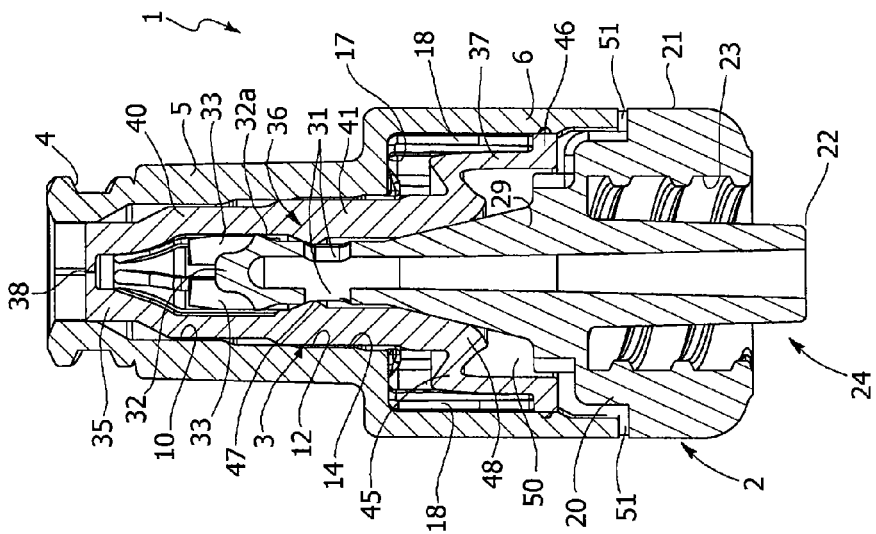
Figure 9:
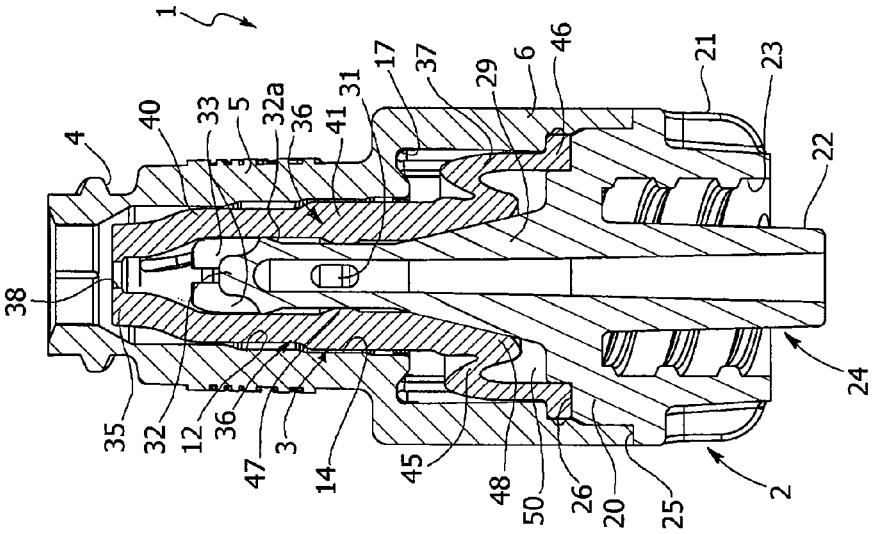
Figure 10:
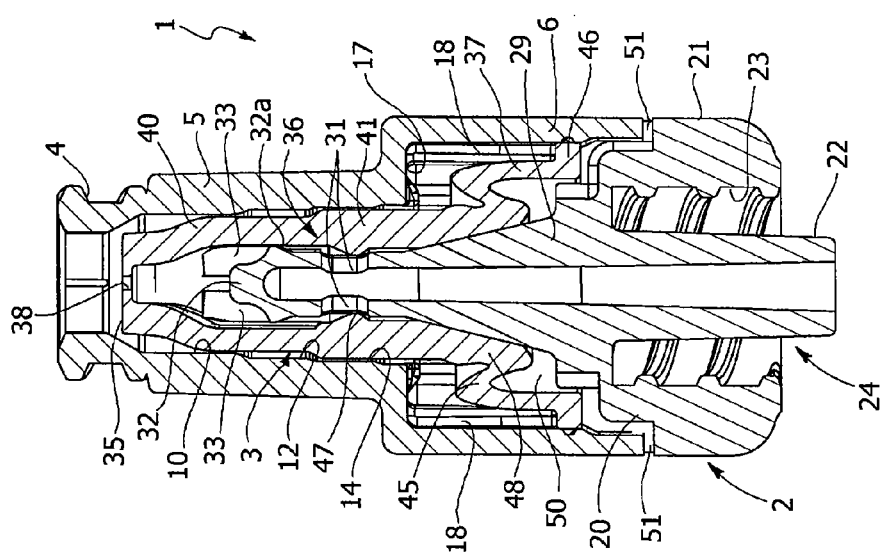
Figure 11:
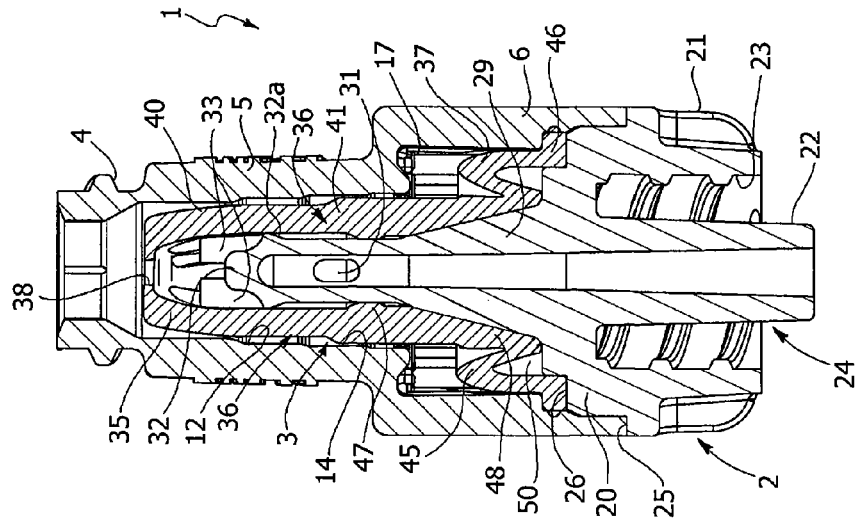
Figure 12:
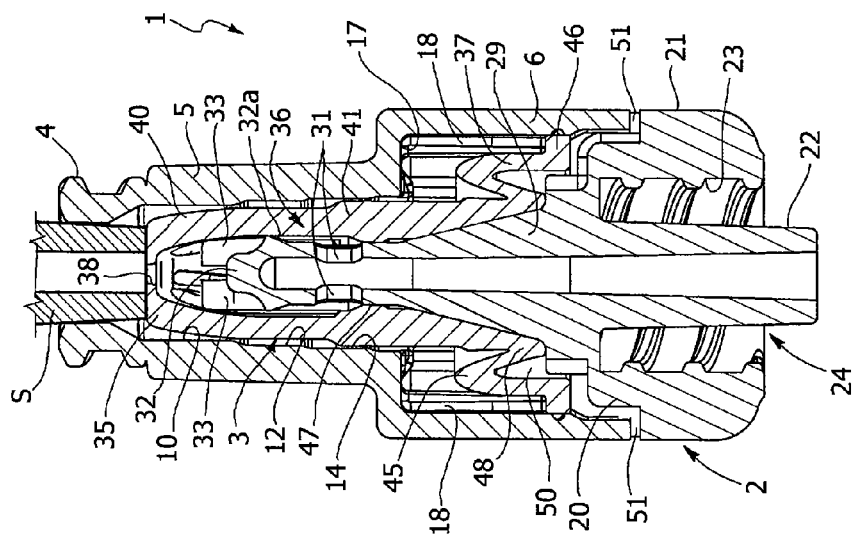
Figure 14:
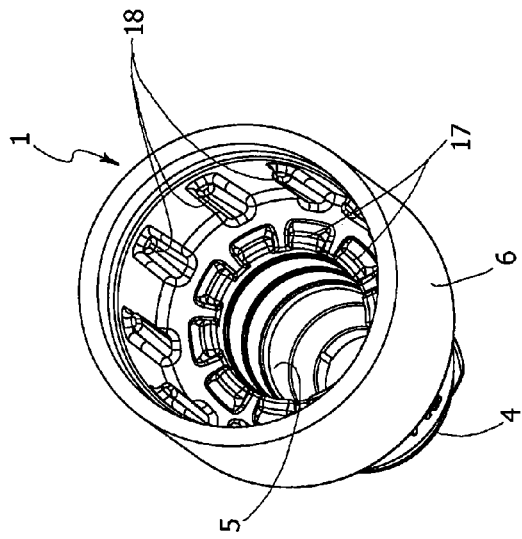
FIG. 14 is a perspective view from beneath of the component of FIG. 13.
Figure 15:
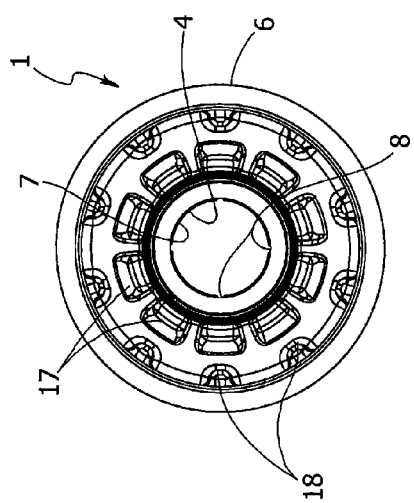
FIG. 15 is a plan view from beneath of the component of FIG. 13.
Figure 13:
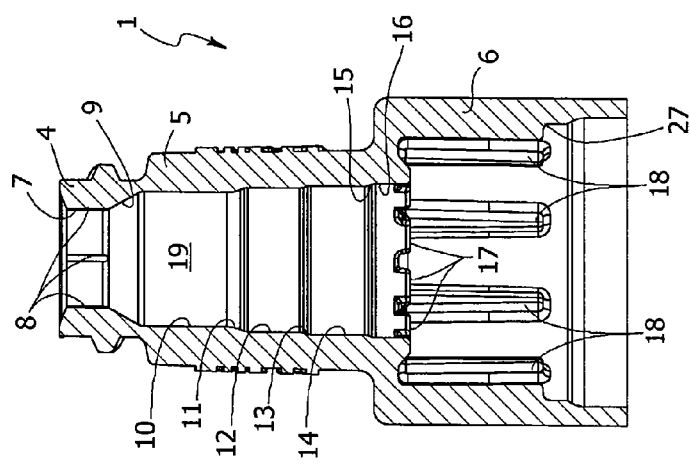
FIG. 13 shows in axial cross section a first component of the valve connector.

As is illustrated in detail in FIGS. 13 to 15, the tubular body 1 has an inlet end 4 formed like a female luer-lock connection member for engagement, in a generally conventional way, with a male luer-lock connection member of an introducer for fluid, constituted, for example, by a needleless syringe, a part of which is designated as a whole by S in FIGS. 3 and 11. The inlet end 4 is connected to a generally cylindrical intermediate portion 5, followed by a final widened portion 6, which is also generally cylindrical.

The internal surface of the inlet end 4 has an initial cylindrical part 7 formed with a series of axial channels 8 and radiused to a portion having the shape of a truncated cone 9. The internal surface of the intermediate part 5 has, in succession, towards the final portion 6, a first cylindrical portion 10, a portion having the shape of a truncated cone 11, a second cylindrical portion 12, a portion having the shape of a truncated cone 13, a third cylindrical portion 14, a portion having the shape of a truncated cone 15, and a fourth cylindrical portion 16 terminating with a ring of front axial projections 17 facing the inside of the enlarged terminal portion 6. The internal surface of the latter is in turn formed with a ring of axial projections 18 projecting radially, the free ends of which define an annular shoulder designated by 27, the function of which will be clarified in what follows.

The cavity of the tubular body 1 is designated as a whole by 19.

The hollow spike 2, illustrated in greater detail in FIG. 16, has a base designated as a whole by 20, formed on the outside with a gripping ring 21 and shaped internally like a male luer-lock connection member with a central tubular shank 22 having a slightly conical outer surface and an internally threaded external shell 23. The connection member 22-23 defines the outlet end of the valve connector 1, designated as a whole by 24.

The base 20 is formed with a first annular flange 25 of larger diameter, for joining the edge of the free end of the widened terminal portion 6 of the tubular body 1, fixed in the way represented in FIGS. 3-12, and an annular flange of smaller diameter 26, the function of which will also be clarified in what follows. Branching off in an integral way from said annular flange 26 is a tubular post 28, preferably but not necessarily coaxial to the shank 22 and in communication with this, including an initial portion within a conical surface 29, divergent towards the outlet end 24 of the connector, followed by a cylindrical portion 30 formed with one, two or more side holes 31, for example in the form of axially elongated slots. The cylindrical portion 30 has, at its free end, a closed tip 32 (clearly visible in FIGS. 3 to 12) facing the inlet end 4 of the tubular body 1 and situated at a certain axial distance therefrom. Projecting from the closed tip 32 is a ring of radial axial projections 33 set at angular distances apart so as to define between them axial-radial channels of flow 34. The end surfaces of the projections 33 facing the inlet end 4 are preferably plane or slightly rounded.

Formed underneath the closed tip 32 is a conical annular surface 32a.

Figure 19:
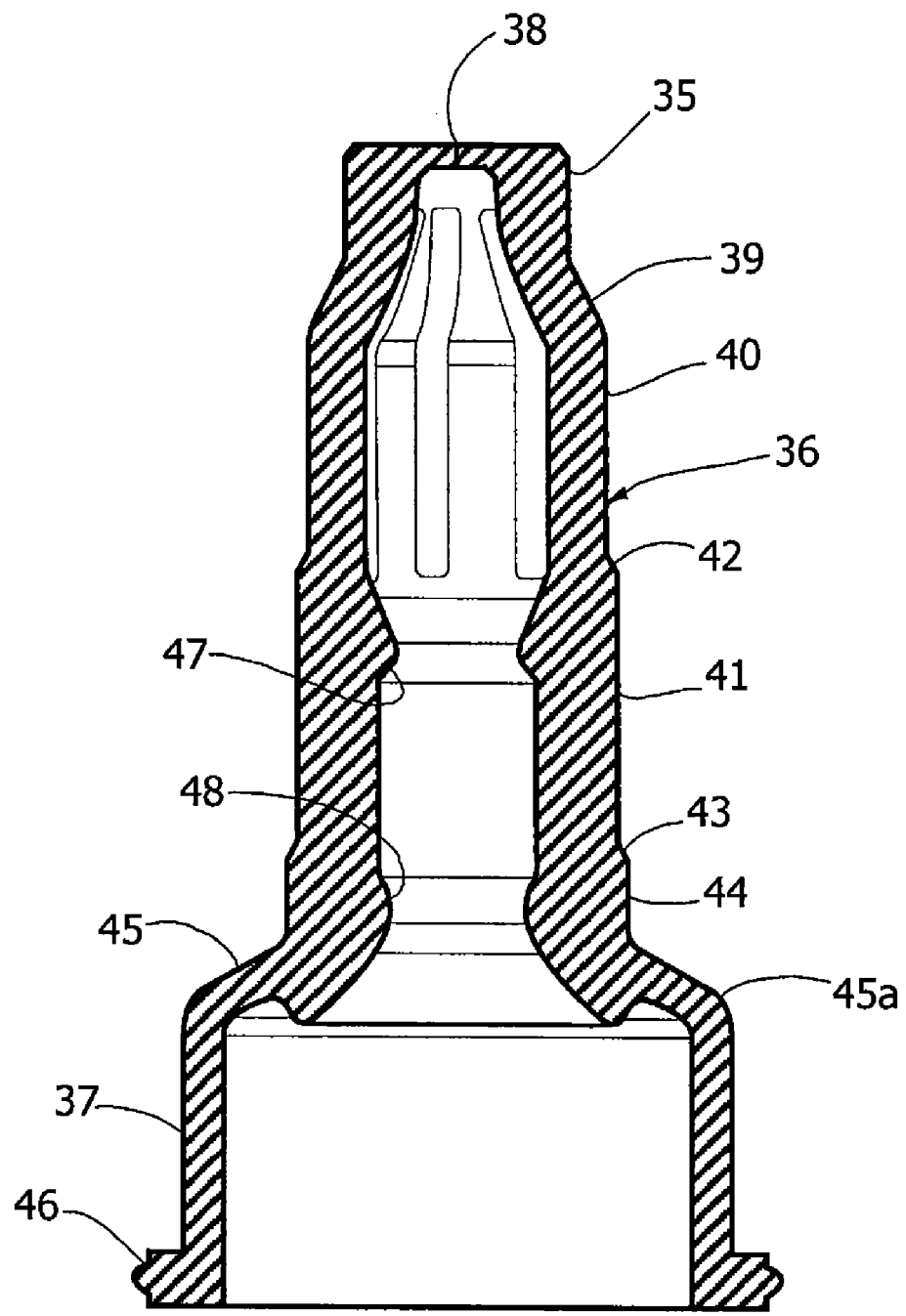
FIG. 19 is an axial cross-sectional view of the component of FIG. 18.
Figure 22:
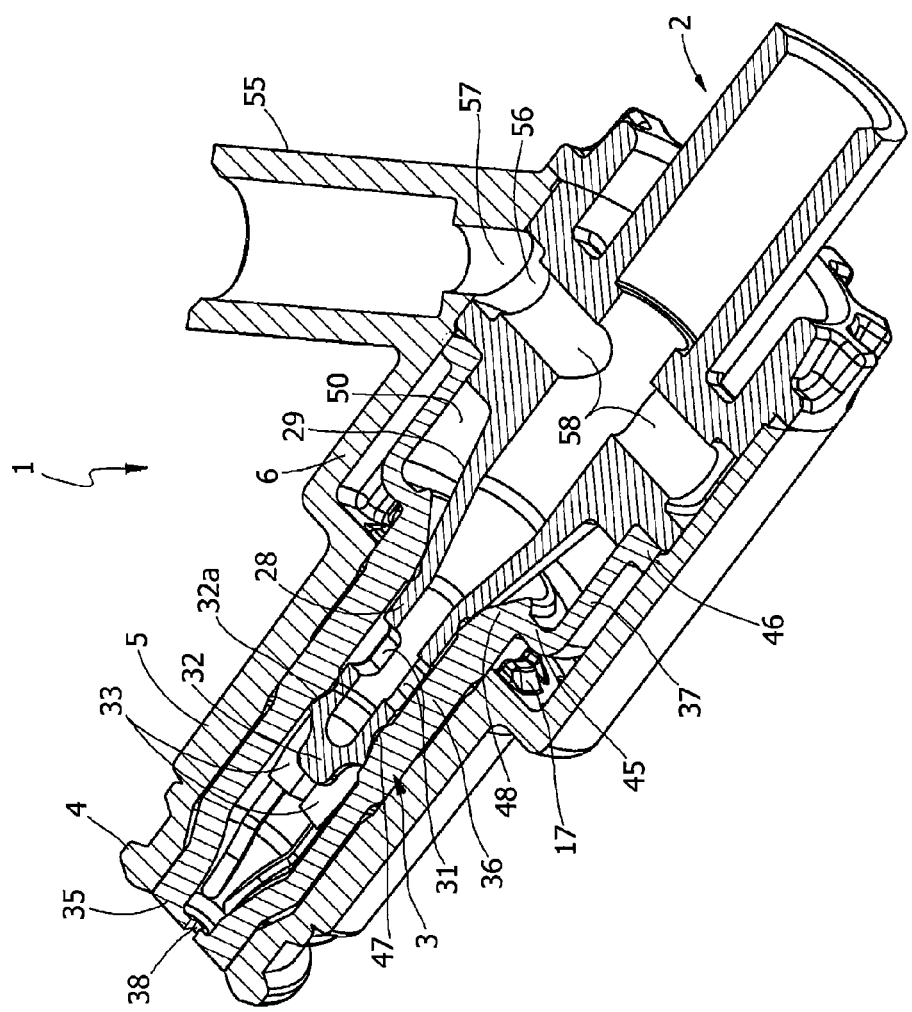
FIG. 22 is a perspective view of the variant of FIG. 21.
Figure 23:
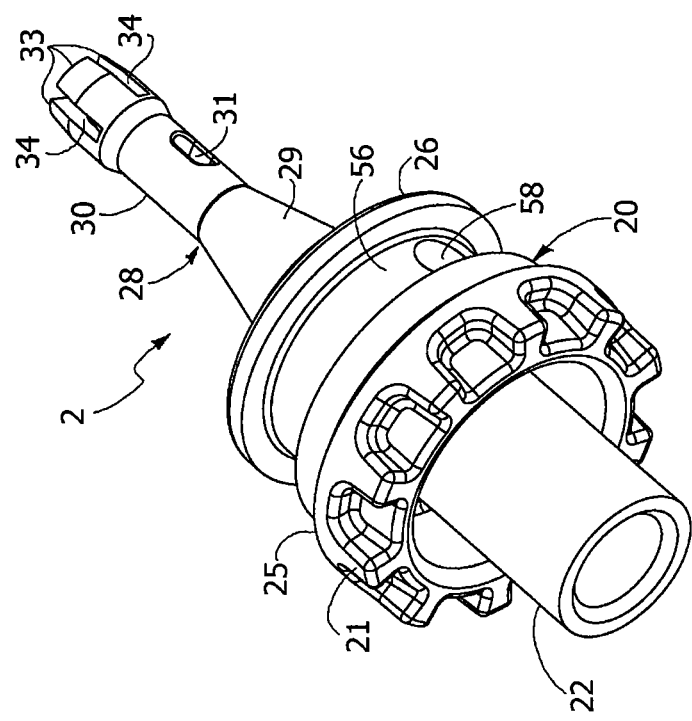
FIG. 23 is a perspective view from above of the second component of the valve connector according to FIGS. 20-22.
Figure 24:
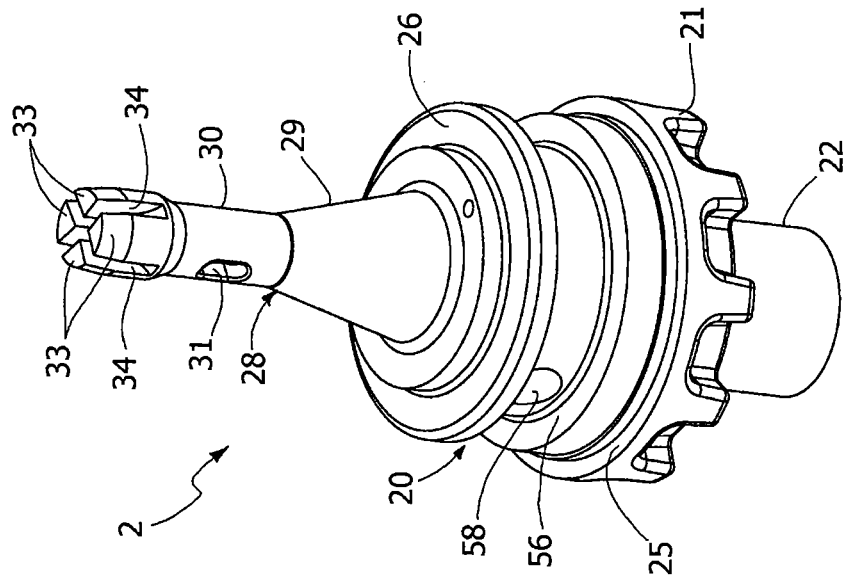
FIG. 24 is a perspective view from beneath of the component of FIG. 23.
Figure 25:
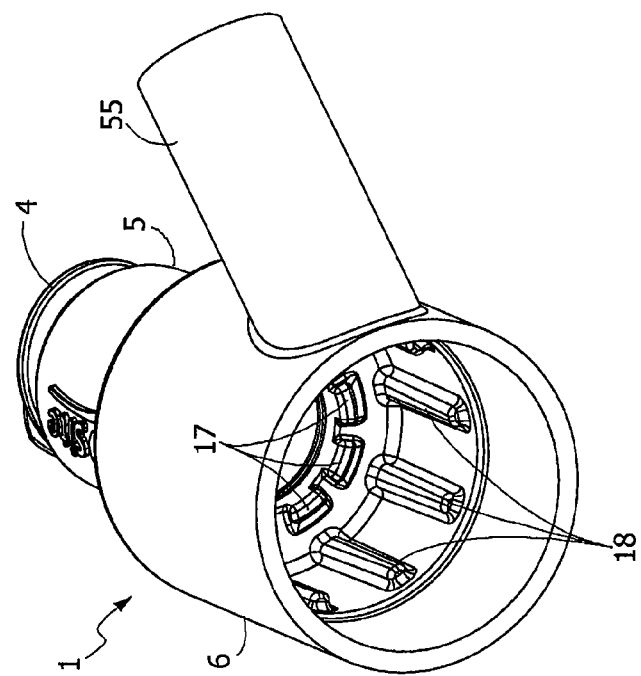
FIG. 25 is an axial cross-sectional view of the second component of FIGS. 23 and 24.
Figure 26:
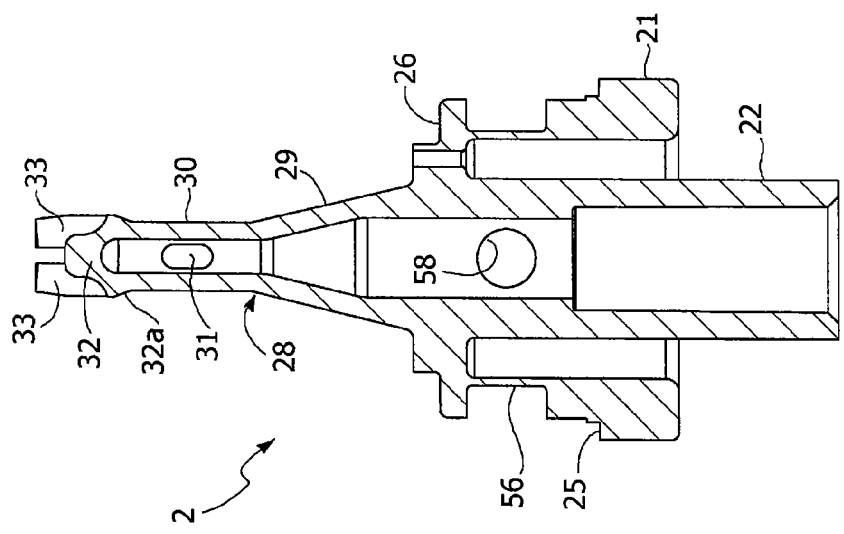
FIG. 26 is a perspective view from beneath of the first component of the valve connector according to FIGS. 20-22.

The sealing member 3 is illustrated in detail in FIGS. 17 to 19. It comprises, in a single piece, an elastic head 35, an elastic hollow element 36, and an elastic base 37. The general shape of the sealing member 3, and in particular its external conformation, corresponds substantially to that of the cavity 19 of the tubular body 1, within which it is housed. Thus, the elastic head 35 has a cylindrical outer surface complementary to the internal surface 7 of the inlet end 4 in such a way as to enable housing thereof, in the way represented in FIGS. 3 and 4, with slight radial play, i.e., without substantial interference, in a condition of closing in which said head 35 is substantially undeformed.

Formed through the head 35 is a pre-slit or axial notch 38, which, in the undeformed condition of closing of the elastic head 35 within the inlet end 4, is maintained gripped as a result of the elasticity of the head 35. In said condition, an anti-bacterial protection barrier is formed between the inside of the valve connector and the outside, ensuring at the time same the possibility of an effective cleaning conventionally performed by means of a swab soaked in a disinfectant.

The head 35 is connected to the elastic hollow element 36 through a portion having the shape of a truncated cone 39, complementary to the conical surface 9 of the tubular body 1. The outer surface of the elastic hollow element 36 in turn has a first cylindrical portion 40, which is radiused to a second cylindrical portion 41 through a portion having the shape of a truncated cone 42. The second cylindrical portion 41 is radiused in turn to the elastic base 37 through a portion having the shape of a truncated cone 43, followed by a cylindrical portion 44. The portions 40, 42, 41, 43 and 44 have shapes complementary to those of the portions 10, 11, 12, 13 and 14-16 of the internal surface of the tubular body 1.

The elastic base 37 has a general cylindrical shape, the external diameter of which substantially corresponds to that defined by the ring of internal axial projections 18 of the terminal portion 6 of the tubular body 1. Said elastic base 37 is radiused to the cylindrical portion 44 of the elastic hollow element 36 through a generally transverse wall 45, which, in the undeformed condition of the sealing member 3 represented in FIGS. 17 to 19, has the shape of a truncated cone.

The elastic base 37 terminates, on the side opposite to the elastic head 35, with an external annular flange 46 by means of which said elastic base 37 is gripped and blocked axially in a fluid-tight way between the annular shoulders 26 and 27, respectively of the base 25 of the hollow spike 2 and of the terminal part 6 of the tubular body 1, in the way represented in FIGS. 3 to 12.

The elastic base 37 and the transverse wall 45 preferably have a wall thickness generally smaller than that of the remaining part of the sealing member 3.

Internally, the sealing member 3 is formed with a first annular projection 47 and with a second annular projection 48, set at axial distances apart from one another and designed to define, with the modalities clarified in what follows, a first fluid-tight member and a second fluid-tight member, respectively.

In the assembled condition of the valve connector according to the invention, the tubular body 1 is fixed to the hollow spike 2, as has been said, in a position corresponding to the annular flange 25 of the base 20 of the latter, with the tubular post 28 that extends coaxially within the cylindrical part 5. The sealing member 3 is in turn contained within the tubular body 1 with the elastic head 35 set, in the way clarified previously, within the inlet end 4, the elastic hollow element 36 housed within the cylindrical part 5 so as to surround the tubular post 28 of the hollow spike 2, and the elastic base 37 housed within the terminal portion 6 of the tubular body 1. As has been said, the annular end flange 46 of the elastic base 37 is gripped axially between the shoulders 26 and 27 of the hollow spike 2 and of the tubular body 1, respectively, with the wall of said elastic base resting against the ring of axial ribbings 18. The transverse wall 45 is adjacent to the ring of front projections 17, so as to be slightly deformed elastically in a generally plane, i.e., radial, condition (represented in FIGS. 3 and 4). The first internal fluid-tight member 47 of the sealing member 3 is set in fluid-tight contact against the conical surface 32a of the tip 32 of the hollow spike 2, thanks to the interaction between the outer cylindrical surfaces 40, 41 of the elastic hollow element 36 and the complementary inner cylindrical surfaces 10, 12 of the hollow body 1, whilst the second fluid-tight member 48 is set in fluid-tight contact against the area of smaller diameter of the conical part 29, thanks to the interaction between the outer cylindrical surface 44 of the elastic hollow element 36 and the complementary inner cylindrical surface 14 of the hollow body 1. The elastic hollow element 36 and the elastic head 35 of the sealing member 3 are normally kept in a condition of slight axial pre-loading within the tubular body 1, and the side holes 31 of the hollow spike 2 are isolated hermetically with respect to the inlet end 4 of the connector, communication of which with the outlet end 24 being thus closed.

Between the elastic base 37 and the wall 35 on the one hand, and the part having the shape of a truncated cone 29 of the hollow spike 2 on the other, there is thus defined an annular chamber 50, which communicates with the outside of the valve connector through one or more passages 51 formed in the base 20 of the hollow spike 2.

Since the annular chamber 50 is in communication with the outside through the passages 51, the pressure inside it is evidently atmospheric pressure.

The condition described above corresponds to fluid-tight closing of the valve connector.

When the end of the needleless syringe or introducer S is resting at the front against the elastic head 35 and hence inserted within the inlet connector 4, in the way represented in FIGS. 3 and 4, the elastic head 35 is pushed axially towards the inside of the connector thanks to the elastic deformation of the sealing member 3 and, more in particular, to the deflection of the wall 45 of the elastic base 37 within the annular chamber 50.

Proceeding with insertion of the introducer S, the wall 45 continues to undergo deflection within the annular chamber 50, undergoing progressive deformation due to tensile stress in the way represented respectively in FIGS. 5-6, 7-8 and 9-10, in which the introducer S has been omitted for reasons of simplicity of illustration.

As a result of the deflection due to tensile stress of the wall 45, the elastic base 37 is compressed and tends, in the area of radiusing with the wall 45, designated as a whole by 45a in FIG. 19, to "roll up" towards the inside of the annular chamber 50, in the way represented schematically in FIGS. 7-8, 9-10 and 11-12.

The elastic head 35 and the elastic hollow element 36 of the sealing member 3 then slide progressively within the tubular body 1 and along the tubular post 28 of the hollow spike 2 in such a way that the first fluid-tight member 47 moves away from the conical surface 32a of the tip 32, whilst the second fluid-tight member 48 slides in a fluid-tight way along the conical part 29.

Simultaneously, the projections 33 of the hollow spike 2 start to interact from inside with the elastic head 35, which (FIGS. 9 and 10) starts to assume an elastically deformed configuration, namely, radially dilated towards the outside, so as to start to open the pre-slit 38.

Following upon complete insertion of the introducer S (FIGS. 11 and 12), the pre-slit 38 is completely opened, whilst the first fluid-tight member 47 sets itself underneath the side holes 31 of the hollow spike 2. The second fluid-tight member 48 has displaced slidably up to the area of larger diameter of the conical part 29 of the hollow spike 2, and the wall 45 is completely deflected and stretched within the annular chamber 50. The valve connector is thus in an opening condition, with the inlet end 4 (and hence the introducer S) in communication with the outlet end 24 through the pre-slit 38, the axial-radial channels 34, the side holes 31, the tubular post 28, and the shank 22.

When the introducer S is extracted from the inlet end 4, the elastic return of the wall 45 and of the sealing member 3 as a whole promptly restores the configuration of closing of the valve connector, in which the elastic head 35 returns into the undeformed condition within the inlet end 4, reclosing the pre-slit 38, and the side holes 31 are again isolated by the fluid-tight members 47 and 48.

FIGS. 20 to 26 illustrate a variant of the valve connector according to the invention. In said variant, in which parts that are identical or similar to the ones already described previously are designated by the same reference numbers, the tubular body 1 of the valve connector is provided with a tubular side Y-connector 55. Said side connector 55 is formed integrally with the terminal cylindrical portion 6 of the tubular body 1, substantially at the height of the base 20 of the tubular spike 2. The base 20 is formed with a circumferential groove 56 closed on the outside in a fluid-tight way by the wall of said cylindrical terminal portion 6, which in this variant has an axial extension slightly greater than that of the preceding embodiment. The groove 56 thus defines an annular chamber, which on the one hand communicates with the side connector 55 through a hole 57, and on the other is connected with the cavity of the spike 2 and with the shank 22, i.e., with the outlet end 24 of the connector, through one or more radial passages 58.

Operation of the valve connector with the Y-connector 55 is altogether identical to what was described previously with reference to FIGS. 3 to 12.

In both of the embodiments described above, the valve connector according to the invention presents, as compared to similar known valve connectors, a series of important advantages: an improved degree of reliability in terms of prompt return of the sealing member into the closed condition even following upon repeated opening; appreciably reduced overall axial dimensions; fabrication with a minimal number of parts, which can be produced in a relatively simple and inexpensive way; capacity of ensuring the substantial absence of overpressures or negative pressure inside the valve connector during the steps of transition between the condition of opening and that of closing.

Of course the details of construction and the embodiments may vary widely with respect to what is described and illustrated herein, without thereby departing from the scope of the present invention, as defined in the ensuing claims.

What is claimed is:

1. A valve connector for medical lines for infusion by means of an introducer of fluid, comprising:
    a tubular body having a cavity, an inlet end provided for engagement of said introducer, and an outlet end;
    a hollow spike set axially within the cavity of the tubular body and having a closed tip facing said inlet end of the tubular body and set at an axial distance therefrom, said hollow spike being in communication with said outlet end and having at least one side hole set at a distance from said closed tip for communication with the cavity of said tubular body; and
    a sealing member including:
        an elastic head having a pre-slit and normally set in a closed condition within said inlet end of the tubular body, in which said pre-slit is closed, said elastic head being displaceable axially against said closed tip of the hollow spike as a result of insertion of said introducer within said inlet end, for interacting with said closed tip to cause an elastically deformed condition of opening of said pre-slit;
        an elastic hollow element joined to said head, set between said tubular body and said hollow spike and having sealing means in contact with said hollow spike for isolating said at least one side hole from the cavity of the tubular body when said head is set in the aforesaid undeformed closed condition, said elastic hollow element including an elastic thrust means tending to maintain said head in said closed condition,
    wherein said elastic thrust means comprises a base part of said sealing member having a generally cylindrical wall set at a radial distance from said hollow spike, said base part joined to said elastic hollow element through a generally transverse annular wall extending substantially perpendicularly relative to a longitudinal axis of said elastic hollow element, said cylindrical wall extending axially between said transverse annular wall and a spike base of said spike,
    said cylindrical wall, said transverse annular wall, said spike base, and a conical surface of said spike bounding an annular chamber between said spike and said cylindrical wall, said annular wall bending into said annular chamber during axial displacement of said elastic head from said closed condition to said open condition, said annular chamber is in fluid communication with an outside of the connector via a passage formed in said spike base, said passage avoiding communication with an interior of said spike;
    said sealing means comprising a first internal annular projection and a second internal annular projection, set at an axial distance apart from one another and arranged axially on opposite sides with respect to said at least one side hole of said hollow spike in the closed condition of said elastic head; and
    said second internal annular projection set in fluid-tight sliding contact against a portion of said conical surface of said hollow spike, the portion of the conical surface bounding said annular chamber and being divergent towards said outlet end of the connector, said second internal annular projection bounding said annular chamber and located immediately between said transverse wall and said portion of said conical surface, and said second internal annular projection directly connected to said transverse wall.

2. The valve connector according to claim 1, wherein said generally transverse wall bends undergoing deformation due to tensile stress.

3. The valve connector according to claim 1, wherein said first annular projection is kept, in said condition of closing of the elastic head, in fluid-tight contact against an annular projection within a conical surface formed in the proximity of said closed tip of said hollow spike.

4. The valve connector according to claim 1, wherein said base part of said elastic thrust means of said sealing member is blocked axially between said tubular body and a base part of said hollow spike.

5. The valve connector according to claim 1, wherein said elastic head of said sealing member is set, in said condition of closing, substantially without interference within said inlet end of said tubular body.

6. The valve connector according to claim 5, wherein said inlet end of said tubular body has an internal wall formed with axial channels.

7. The valve connector according to claim 1, wherein said elastic hollow element of said sealing member has an outer wall with axial portions having a cylindrical surface connected to one another by portions having the shape of a truncated cone, and wherein said tubular body has, at an area corresponding to said elastic hollow element, an internal surface of complementary shape.

8. The valve connector according to claim 1, wherein said generally transverse annular wall of said sealing member has a thickness that is substantially smaller than that of said elastic hollow element.

9. The valve connector according to claim 1, wherein said base part of said sealing member is housed within a widened cylindrical portion of said tubular body formed with a ring of axial projections projecting radially towards said base part.

10. The valve connector according to claim 9, wherein said widened cylindrical portion of said tubular body is formed with a ring of axial projections projecting at the front towards said generally transverse annular wall of said sealing member.

11. The valve connector according to claim 1, wherein said closed tip of said hollow spike is shaped so as to cause said elastic head of said sealing member to assume said condition of opening without traversal of said pre-slit.

12. The valve connector according to claim 11, wherein said closed tip of said hollow spike has a plurality of axial projections set at angular distances apart from one another and delimiting channels of flow facing said inlet end of said tubular body.

13. The valve connector according to claim 1, wherein said outlet end consists of a male luer-lock connection element formed integrally with said hollow spike.

14. The valve connector according to claim 1, wherein said tubular body is formed with a tubular side Y-connector.

15. The valve connector according to claim 14, wherein said tubular Y-connector communicates with said outlet end of the connector through an annular chamber in communication with the inside of said hollow spike downstream of said at least one side hole.

16. The valve connector according to claim 15, wherein said annular chamber is formed by a circumferential groove of an enlarged portion of said hollow spike closed on the outside by said tubular body and connected to said outlet end of the connector through at least one radial passage of said enlarged portion.

17. The valve connector according to claim 1 wherein said cylindrical wall extends along and abuts an inner surface of said body.

18. The valve connector according to claim 1 wherein said spike comprises a cylindrical portion connected to said conical portion and closer to said inlet end than said conical portion, said first projection abutting said cylindrical portion.

* * * * *